(12) United States Patent
Wöhrle et al.

(10) Patent No.: US 8,066,511 B2
(45) Date of Patent: Nov. 29, 2011

(54) ASYMMETRICAL DENTAL IMPLANT

(76) Inventors: Peter Wöhrle, Newport Beach, CA (US); Hatem Tadros, Yorba Linda, CA (US)

( * ) Notice: Subject to any disclaimer, the term of this patent is extended or adjusted under 35 U.S.C. 154(b) by 430 days.

(21) Appl. No.: 12/050,795

(22) Filed: Mar. 18, 2008

(65) Prior Publication Data
US 2009/0239195 A1    Sep. 24, 2009

(51) Int. Cl.
*A61C 8/00* (2006.01)
(52) U.S. Cl. ........................................... 433/174
(58) Field of Classification Search .......... 433/172–176, 433/20.1, 202.1, 215, 220, 221, 201.1
See application file for complete search history.

(56) References Cited

U.S. PATENT DOCUMENTS

| | | | |
|---|---|---|---|
| 5,779,480 A * | 7/1998 | Groll et al. ..................... | 433/173 |
| 6,174,167 B1 * | 1/2001 | Wohrle ......................... | 433/173 |
| 2004/0185420 A1 * | 9/2004 | Schulter et al. ............... | 433/173 |
| 2005/0014108 A1 * | 1/2005 | Wohrle et al. ................ | 433/173 |
| 2006/0003291 A1 * | 1/2006 | Hall ............................. | 433/174 |
| 2006/0194170 A1 * | 8/2006 | Wohrle et al. ................ | 433/173 |
| 2007/0298379 A1 * | 12/2007 | D'Alise ........................ | 433/174 |
| 2009/0155744 A1 * | 6/2009 | Jandali ......................... | 433/174 |

* cited by examiner

*Primary Examiner* — Cris L Rodriguez
*Assistant Examiner* — Heidi M Eide
(74) *Attorney, Agent, or Firm* — Knobbe Martens Olson & Bear, LLP (57) ABSTRACT

A dental implant is provided for supporting a dental prosthesis. The implant can include a body having an outer surface, an apical end, and a coronal portion. The dental implant can include at least one thread located on at least a portion of the outer surface of the body. The dental implant can include a collar having a top surface that defines two peaks and two valleys, where the one valley is more coronal than the second valley.

22 Claims, 7 Drawing Sheets

ASYMMETRICAL DENTAL IMPLANT

BACKGROUND

1. Field of the Invention

The present invention generally relates to dental restorations, and more specifically, to dental implants.

2. Description of the Related Art

Implant dentistry involves the restoration of one or more teeth in a patient's mouth using artificial components. Such artificial components typically include a dental implant and a prosthetic tooth and/or an abutment that is secured to the dental implant. Generally, the process for restoring a tooth is carried out in three stages.

The dental implant is typically fabricated from pure titanium or a titanium alloy. The dental implant typically includes a body portion and a collar. The body portion is configured to extend into and osseointegrate with the alveolar bone. The top surface of the collar typically lies flush with the crest of the jawbone bone. The abutment (e.g., a final abutment) typically lies on the top surface and extends through the soft tissue, which lies above the alveolar bone. Recently, some dental implants have collars that extend above the crest of the jawbone and through the soft tissue.

Implants of various tapers and with various thread profiles are known in the art. For example, U.S. Pat. No. 5,427,527 describes a conical implant design that is placed into a cylindrical osteotomy site in order to induce bone compression at the coronal aspect of the implant, i.e. at its widest end. Other thread profiles and patterns are known in the art. The most common design involves a symmetrical, V-shaped appearance such as that illustrated in U.S. Pat. No. 5,897,319. A variable thread profile is disclosed in U.S. Pat. Nos. 5,435,723 and 5,527,183 which is mathematically optimized for stress transfer under occlusal loads. U.S. Pat. Nos. 3,797,113 and 3,849,887 describe dental implants with external thread-like features having a flat shelf facing the coronal end of the implant.

While such prior art dental implants have been successful, there is a continuing desire to improve a dental implant's ability to osseointegrate with the alveolar bone and to improve the stability of the dental implant within the alveolar bone. For example, U.S. Pat. No. 6,174,167 discloses an implant with a scalloped bone apposition surface and/or a scalloped top surface. Such an implant is configured to better maintain hard and soft-tissue in the area where the implant exits from the bone-tissue and transverses the soft-tissue. More particularly, such implants are designed so that areas intended for hard- and soft-tissue apposition exhibit a scalloped appearance, including convex and/or concave patterns that approximate the naturally occurring bone morphology. While representing an improvement, there is a desire to improve upon the implants of the '167 patent. In particular, in certain clinical setting, it may be difficult to align the scalloped surfaces of the implant with the hard and soft tissue of the patient.

SUMMARY OF THE INVENTION

An embodiment disclosed herein is a dental implant for supporting a dental prosthesis comprising a body. The body can comprise an outer surface, a apical end, and a coronal portion. The dental implant can also include at least one thread located on at least a portion of the outer surface of the body. The thread can include a coronal flank and a apical flank. The thread can also include a face that extends between the coronal flank and the apical flank. The dental implant can also include a first helical groove formed on the face and a second helical groove formed on the body.

Another embodiment is a dental implant for supporting a dental prosthesis comprising a body. The body can comprise an outer surface, a apical body portion, and a coronal body portion. The dental implant can also include at least one thread. The thread can comprise a apical thread portion extending over the apical body portion and a coronal thread portion extending over the coronal body portion. The thread can comprise a coronal flank and a apical flank. The thread can further comprise a face extending between the coronal flank and the apical flank wherein the face increases in thickness from the apical thread portion to the coronal thread portion. The dental implant can also include a groove located on the face of at least a portion of the coronal thread portion.

Further embodiments of the invention are defined by the dependent claims. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

The abovementioned and other features of the inventions disclosed herein are described below with reference to the drawings of the preferred embodiments. The illustrated embodiments are intended to illustrate, but not to limit the inventions. The drawings contain the following figures.

DETAILED DESCRIPTION OF THE PREFERRED EMBODIMENTS

FIGS. 1A-1D illustrate an embodiment of a dental implant 20. In this embodiment, the implant 20 comprises an implant body 32, which includes a threaded portion 34 and a collar 36. The implant 20 may be made of titanium, although other materials may be used, such as various types of ceramics. The threaded portion 34 can include a thread 38 that is located on a root surface 40 of the threaded portion 34. As will be explained below, although the illustrated embodiment includes a single thread 38 with a single lead that extends helically around the implant, modified embodiments may include more threads (e.g., double or triple lead threads). In addition, as explained below, the root surface 40 and/or an outer surface formed by the face or tip of the thread 38 can taper inwardly with respect the apical direction and a longitudinal axis of the implant 20. However, in other embodiments, the root surface 40 and/or an outer surface formed by the face or tip of the thread 38 can be substantially cylindrical or otherwise shaped. The dental implant 20 can comprise a coronal end 22, a coronal portion 26 generally adjacent the coronal end 22, an apical end 24 and an apical portion 28 generally adjacent the apical end 24, and a central portion 27 between the coronal portion 26 and the apical portion 28.

In the illustrated embodiment, the implant body 32 includes a bone apposition surface 41 that is configured to promote osseointegration. In one embodiment, the bone apposition surface 41 is configured to promote osseointegration by increasing the surface area of the implant body 32. In this regard, the bone apposition surface 41 can be formed by roughening the implant body 32 in several different manners, such as, for example, by acid-etching, grit blasting, and/or machining. Alternatively, the bone apposition surface 41 can be formed by coating the lower surface with a substance in order to promote osseointegration. In some embodiments, this may result in decreasing or increasing the surface area of the implant body 32. Calcium phosphate ceramics, such as tricalcium phosphate (TCP) and hydroxyapatite (HA) are examples of materials that can enhance osseointegration by changing the chemistry of the outer surface 40. In other embodiments, the outer surface 40 can comprise macroscopic structures, such as, for example, threads, micro-threads, indentations, and/or grooves that are configured to promote osseointegration and can be used alone or combined with the roughening and/or the coatings described above. In one embodiment, the outer surface 40 comprises a microstructure surface, such as a highly crystalline and phosphate enriched titanium oxide microstructured surface with open pores in the low micrometer range. An example of such a surface is sold under the trademark TiUnite™ by Nobel Biocare AB. In another embodiment, the implant body 32 can be formed from a zirconium ceramic or other ceramic material and can be coated with porous zirconium to provide a microstructure surface. In another embodiment, the microstructure surface can be coated with a substance configured to promote osseointegration (such as BMP).

Figure 1A:
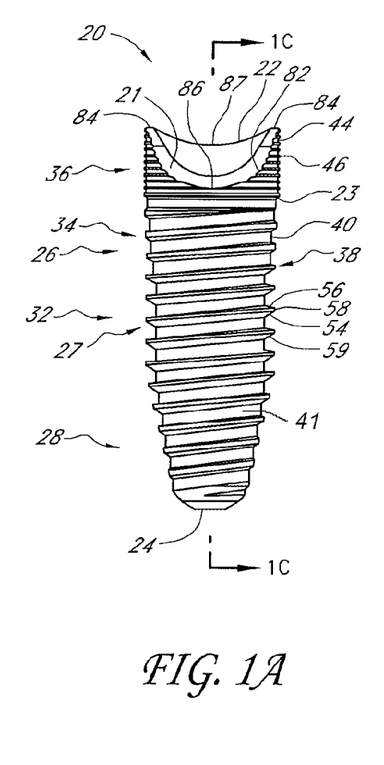
FIG. 1A is a front view of a dental implant in accordance with an embodiment of the present invention.

With continued reference to FIG. 1A, the collar 36 can lie above the threaded portion 34 and, in the illustrated embodiment, can be integrally formed with or permanently affixed to the threaded portion 34. The collar 36 can be defined at least in part by a sidewall 44. In the illustrated embodiment, the sidewall 44 includes a plurality of circular and/or semicircular grooves 46 that are positioned circumferentially around the sidewall 44 of the collar 36. The circular and/or semicircular grooves 46 can provide additional growth surface for bone tissue. Thus in one embodiment, the collar 36 is configured to lie within the patient's bone. In one embodiment, the circular and/or semicircular grooves 46 have a width of about 150 microns and a depth of about 50 microns. The grooves 46 can be sized so that the plurality of grooves 46 occupies a substantial portion of the collar 36. In the illustrated embodiment of FIG. 1A, a plurality of grooves 46 are shown as occupying a substantial portion of the collar 36 (e.g., greater than 50% of a total area). In modified embodiments, the collar 36 can be provided with more, less or no grooves and/or grooves with different dimensions and configurations. In other embodiments, circumferential protrusions or microthreads can be provided on the collar 36. In general, such structures on the collar 36 are advantageously configured to load the harder cortical bone through which the implant 20 is inserted but to a lesser extent as compared to the thread 38 of the implant 20, which can be configured to engage the spongy cancellous bone positioned below the cortical bone. In other embodiments, the collar 36 can be non-cylindrical with, for example, an inwardly tapered or an outwardly tapered side wall 44.

In the description herein, reference will be made to various structures that "taper" "inwardly." Unless otherwise specified, tapering inwardly means that the surface of the referenced structure generally lies closer to the longitudinal center of the dental implant 20 as the structure moves towards the apical end 24 of the implant 20. Accordingly, "tapering outwardly" means that the surface of the referenced structure generally lies further from the longitudinal center of the implant 20 as the structure moves to the apical end 24 of the implant 20.

In the embodiment shown in FIGS. 1A-1D, the thread 38 comprises a apical flank 54 and a coronal flank 56 that are connected by a face 58. The base of the thread comprises the root surface 40. As mentioned above the illustrated dental implant 20 includes a thread 38 that begins at the apical end 24 and progresses towards the coronal portion 26 along the apical portion 28. It will be appreciated that, although the illustrated embodiment shows a single thread 38, other suitable numbers of threads may also be used, such as two or three.

Figure 1B:
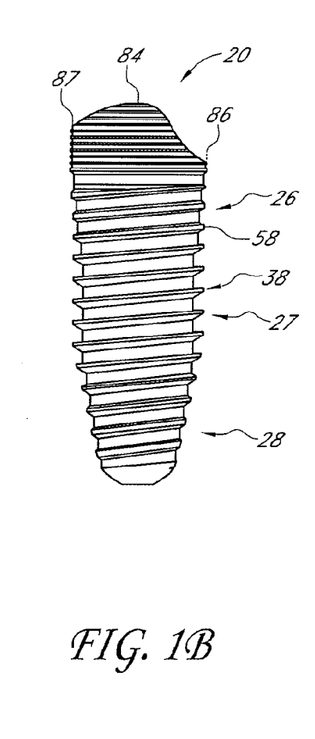
FIG. 1B is a side view of the dental implant of FIG. 1A.

As illustrated in FIG. 1B, in some embodiments of the implant 20 the width of the face 58 of the thread 38 is greater within the coronal portion 26 and the apical portion 28 relative to the face 58 of the thread 38 in the central portion 27. In other words, the width of the face 38 of the thread 38 is narrower in the central portion 27 of the implant 20. In some embodiments, the width of the face 58 of the thread 38 in the central portion 27 can be between about 0.02 to about 0.3 mm, or preferably between about 0.08 mm to about 0.12 mm. In addition, in some embodiments the depth of the thread 38 is greater in the central portion 27 and the depth of the thread 38 is shallower in the coronal portion 26 and the apical portion 28. In some embodiments, the depth of the thread 38 in the central portion 27 is between about 0.1 mm to about 0.5 mm, or between about 0.2 mm to about 0.4 mm, or about 0.3 mm. In some embodiments, the thread 38 pitch is between about 0.4 mm to about 1.0 mm, or between about 0.6 mm to about 0.8 mm, or about 0.7 mm. In some embodiments, the coronal flank 56 extends substantially perpendicularly from the longitudinal axis of implant 20. In some embodiments, the coronal flank 56 extends at an angle between about 45 degrees to about 90 degrees, or between about 60 degrees to about 90 degrees, or between about 75 degrees to about 90 degrees from the longitudinal axis of the implant 20. In some embodiments, the apical flank 54 is oriented at an angle between about 15 degrees to about 45 degrees, or between about 25 degrees to about 35 degrees, or about 30 degrees with respect to the coronal flank 56.

Figures 1C, 1D:
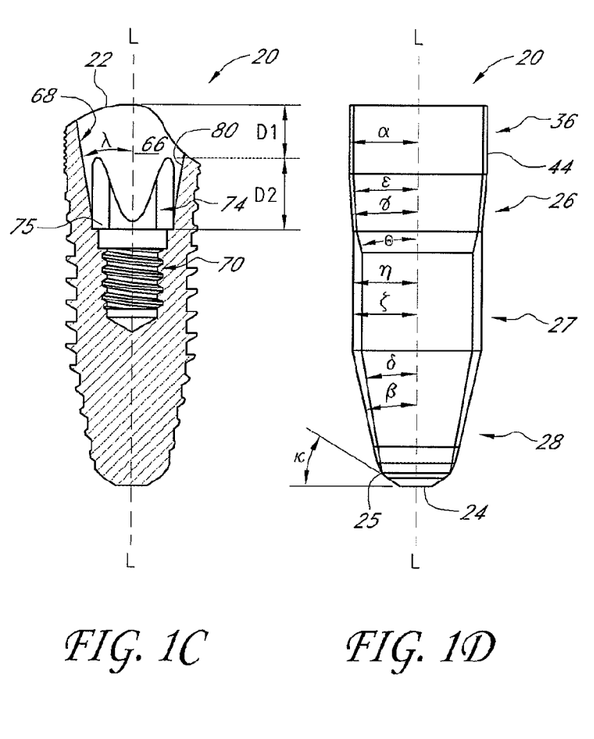
FIG. 1C is a cross-sectional side view of the dental implant of FIG. 1A taken along line 1C-1C.
FIG. 1D is a schematic view of the dental implant of FIG. 1A illustrating both the thread profile and the implant body profile.

As illustrated in FIG. 1D, the implant body 32 can define a plurality of different angles with respect to the longitudinal axis L: a first angle $\alpha$ can be defined by the sidewall 44 of the collar 36 as described above; a second angle $\beta$ can be defined by the face 58 of the thread 38 on the apical portion 28 of the body 32; a third angle $\gamma$ can be defined by the face 58 of the thread 38 on the coronal portion 26 of the body 32; a fourth angle $\delta$ can be defined by the root surface 40 on the apical portion 28 of the body 32; a fifth angle ε can be defined by the root surface 40 on the coronal portion 26 of the body 32; a sixth angle ζ can be defined by the face 58 of the thread 38 on the central portion 27 of the implant body 32; a seventh angle η can be defined by the root surface 40 in an central portion 27 of the implant body 32 in between the coronal portion 26 and the apical portion 28; an eighth angle θ can be defined by the root surface 40 in a transition zone between the coronal portion 26 and the central portion 27; and a ninth angle κ can be defined by the substantially perpendicular apical end 24 and the apical tip portion 25.

Although the illustrated embodiment utilizes the aforementioned angle relations, other suitable relations may be used. Such suitable relations may comprise a thread 38 in which the face 58 are not conical and define a generally cylindrical shape and/or where the face 58 of the thread 38 that defines a conical angle that closely matches the conical angle of the threaded portion 34 of the implant body 32. In still other embodiments, the angle defined by the face 58 of the thread 38 and/or the angle defined by the root surface 40 can be generally parallel to the longitudinal axis of the implant 20 such that they are substantially cylindrical.

As best seen in FIG. 1C, the dental implant 20 can also comprise a cavity or internal connection interface 66 that is open at the coronal end 22 of the dental implant 20. In the illustrated embodiment, the cavity 66 comprises a conical chamber 68, an interlock recess 74 and a threaded chamber 70. The conical chamber 68 and interlock recess 74 can be configured to receive an abutment and the threaded chamber 70 can be configured to receive a coupling screw (not shown).

The threaded chamber 70 can be located generally below the conical chamber 68. As was mentioned above, the threaded chamber 70 can be configured to receive a coupling screw that is configured to attach an abutment to the implant 20.

Although the particular embodiment shown in FIGS. 1A-1D has been shown with a conical chamber 68 and a generally hexagonal shaped interlock recess 74, other suitable shapes and styles of recesses may also be used (e.g., square, octagonal, non-round, and other shapes). Furthermore, it may be appreciated by one skilled in the art, that some embodiments of the dental implant 20 may omit a cavity 66 all together and may use an external coupling device (e.g., an external hex) and/or an integrally formed abutment. With respect to the illustrated embodiment, additional details and modified embodiments of the cavity 66 and other features can be found in Applicant's co-pending applications, U.S. application Ser. No. 11/739,034 filed on Apr. 23, 2007, entitled "DENTAL IMPLANT" and U.S. application Ser. No. 11/739, 024 filed on Apr. 23, 2007, entitled "DENTAL IMPLANT AND DENTAL COMPONENT CONNECTION," the entirety of which are also incorporated herein by reference.

The illustrated cavity 66 is advantageously configured to provide an enhanced connection interface and to provide flexibility such that the implant 20 can mate with multiple types of dental components. In particular, as noted above, the conical chamber 68 comprises a side wall that tapers inwardly with respect to the longitudinal axis L of the implant 20 providing a wider initial opening for the cavity 66. With reference to FIG. 1C, the particular geometry of the conical chamber 68 defines a conical half angle X with respect to the longitudinal axis L. In one embodiment, the conical half angle is between about 5 degrees and about 20 degrees. That is, the angle between the inner wall 80 of the conical chamber 68 and a longitudinal center line L preferably is between about 5 degrees and about 20 degrees. The conical half angle can also be between about 10 degrees and about 20 degrees. In one embodiment, the conical half angle is about 12 degrees.

In one embodiment, the ratio between the length (d1) of the conical portion 68 and the length (d2) the interlock recess 74 is about 1:1. In one preferred embodiment, the depth (d1) of the conical portion 68 is about 2 mm and the depth (d2) of the interlock recess 74 is about 2 mm. As shown in FIG. 1C, the length (d1) of the conical portion 68 is a distance measured in a vertical direction from the top surface 21 of the implant 20 to the portion of the socket 66 in which the tapered surfaces 80 of the conical portion 68 terminate. The length (d2) of the interlock recess 74 is measured in a vertical direction from the end of the conical portion 68 to the end of the interlock recess 74. The ratios and length of the conical portion 68 and the depth and length of the interlock recess 74 advantageously combine the benefits of a sufficiently long tapered connection to provide an effective seal with a sufficiently long interlock recess 74 such that a sufficient driving torque can be transmitted to the implant 20, when the implant is driven into the patient.

As illustrated in FIGS. 1A and 1B, the collar 36 includes a top surface 21. In the illustrated embodiment, a top edge 82 of the top surface 21 has a curved or scalloped shape with at least one and more preferably two peaks 84, a buccal valley 86 and a lingual valley 87 that follow or at least closely approximate the shape of the naturally occurring contours of a patient's bone-tissue morphology. The buccal valley 86 is configured to face the cheek and the lingual valley 87 is configured to face the tongue. It should also be appreciated that in other embodiments, the peaks 84 and valleys 86 and 87 may be approximated by various combinations of straight and/or curved lines that follow or at least closely approximate the shape of the naturally occurring contours of a patient's bone-tissue morphology. In the illustrated embodiment, the bone apposition surface 41 extends substantially up to the top edge 82. In this manner, the bone apposition surface 41 has an edge or boundary that corresponds with the top edge 82 and thus has the same curved or scalloped shape. In another embodiment, the bone apposition surface 41 can extend onto the top surface 21 of the implant 10. In one arrangement, the bone apposition surface 41 can cover the entire or substantially the entire top surface 21 or only a portion thereof. In still another embodiment, the top surface 21 or a portion thereof can be covered or treated to promote soft-tissue growth.

In the illustrated arrangement, the buccal valley 86 of the top edge 82 lies slightly above or at the collar/implant interface 23. The peaks 84 may lie approximately 1-5 millimeters above the buccal valley 86. In one embodiment, the peaks 84 lie approximately 2 millimeters above the buccal valley 86. The peaks 84 may lie approximately 0.25-2 millimeters above the lingual valley 87. In one embodiment, the peaks 84 lie approximately 1 millimeters or between about 0.7-0.9 millimeters above the lingual valley 87.

As illustrated in FIGS. 1A and 1B, the buccal valley 86 is more apical than the lingual valley 87. In the context of this application, more apical means that the most apical point on the buccal valley 86 is lower than the most apical point on the lingual valley 87. In other embodiments, the lingual valley 87 can be more apical than the buccal valley 86. In addition, as illustrated in FIG. 1B, the curvature of the top edge 82 between the peak 84 and the lingual valley 87 is convex in shape while the curvature of the top edge 82 between the peak 84 and buccal valley 86 is concave in shape. As illustrated in FIG. 1B, in some embodiments the peaks 84 are located about in the middle between the buccal valley 86 and the lingual valley 87. In other embodiments, the peaks 84 can be located closer to either the buccal valley 86 or the lingual valley 87.

This configuration of the top edge 82 and the peaks 84 and valleys 86 and 87 result in an asymmetrical dental implant 20 that is well suited for matching asymmetrical bone-tissue morphologies, resulting in an aesthetically pleasing dental implant 20. It should be appreciated that in modified embodiments the peaks 84 and valleys 86 and 87 may have different heights. That is, the two peaks 84 may have different heights as compared to each other. In a similar manner, the two valleys 86 and 87 may have different heights as compared to each other, as described above for example. In this manner, the implant 10 can be placed in situations where the bone ridge has an asymmetrical shape with the buccal side being typically lower.

Figure 2A:
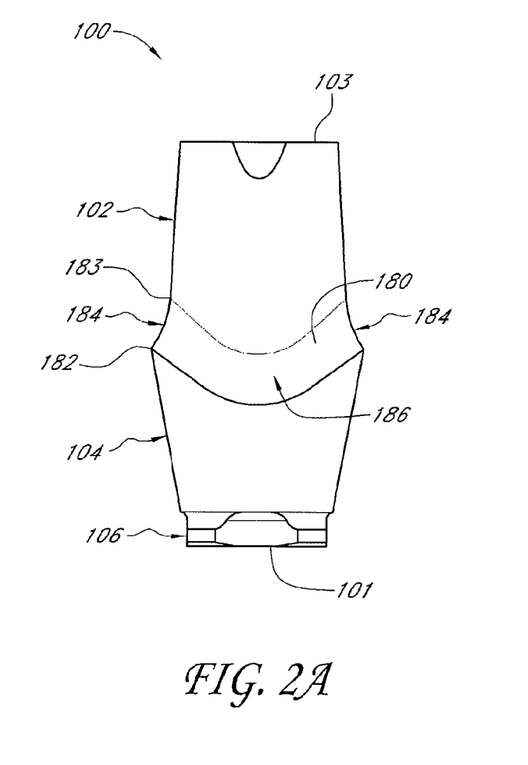
FIG. 2A is a front view of an embodiment of an abutment which is configured to mate with the implant of FIG. 1A.
Figure 2B:
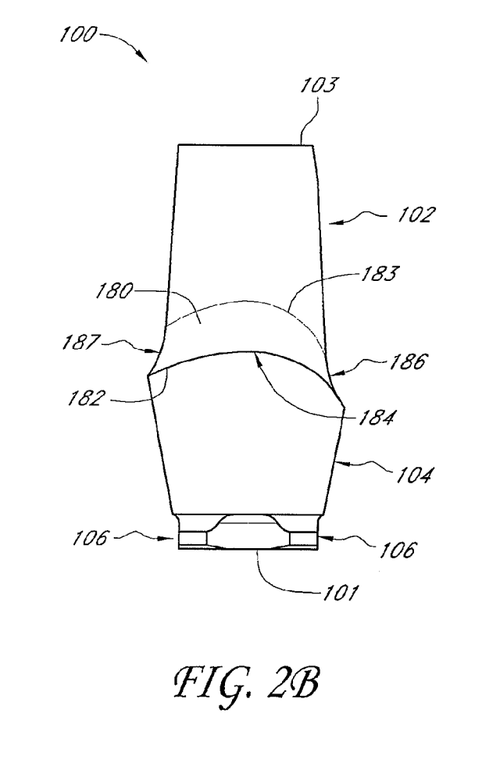
FIG. 2B is a side view of the abutment of FIG. 2A.

FIGS. 2A and 2B illustrate an embodiment of an abutment 100 that is configured to mate with the implant 20 described above. As will be explained below, the abutment 100 is one example of a variety of dental components, such as, for example, a healing cap, impression coping, a temporary healing abutment, or a final abutment that can be configured to be attached to the implant 20. Additional details regarding the illustrated embodiment and regarding modified embodiments of the abutment 100 and other mating components can be found in Applicant's co-pending applications, U.S. application Ser. No. 11/739,034 filed on Apr. 23, 2007, entitled "DENTAL IMPLANT" and U.S. application Ser. No. 11/739,024 filed on Apr. 23, 2007, entitled "DENTAL IMPLANT AND DENTAL COMPONENT CONNECTION," the entirety of which are also incorporated herein by reference. The abutment 100 can be made of dental grade titanium; however, other suitable materials such as various types of ceramics can also be used.

Figure 2C:
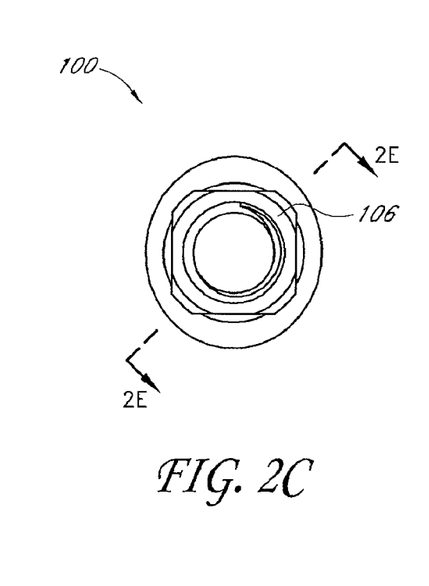
FIG. 2C is a bottom view of the abutment of FIG. 2A.

As seen in FIGS. 2A-2E, the abutment 100 having a apical end 101 and a coronal portion 103 can include a shaped portion 102, a conical portion 104, and an interlock portion 106. As illustrated in FIG. 2C, the interlock portion 106 comprises a generally hexagonal shape that is sized to fit within the interlock recess 74 of the dental implant 20. Although the particular embodiment of the abutment 100 has been illustrated with a generally hexagonal interlock portion 106 other suitable shapes may also be used. Such alternative suitable shapes may comprise other shapes configured to mate with interlock recess 74 and to prevent rotation of the abutment 100.

Figure 2D:
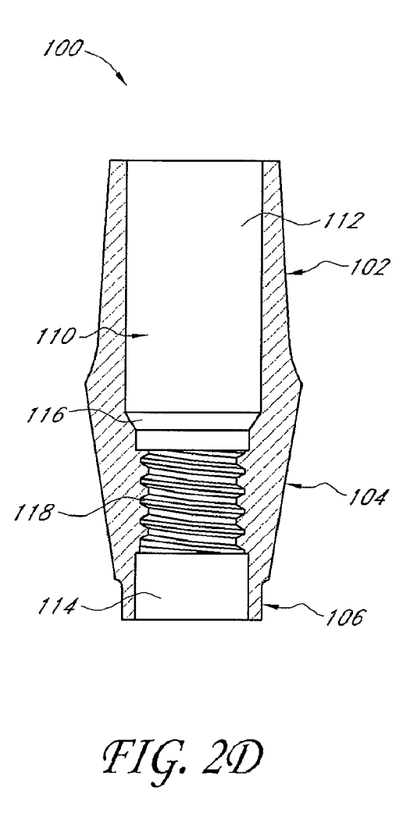
FIG. 2D is a cross-sectional front view of the abutment of FIG. 2A.
Figure 2E:
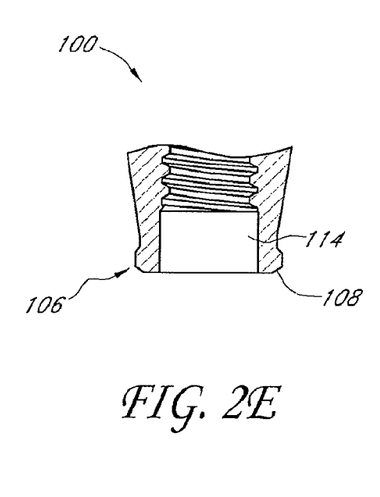
FIG. 2E is a cross-sectional view of the bottom portion of the implant of FIG. 2C taken along line 2E-2E.

With continued reference to FIGS. 2A, 2B and 2D, the conical portion 104 is configured to be at least partially inserted into the conical chamber 68. Above the conical portion 104, the abutment 100 comprises the shaped portion 102, which in the illustrated embodiment is shaped such that the abutment 100 is a final abutment. It should be appreciated that the shaped portion 102 can be shaped into any desirable shape such as that of a temporary abutment, healing abutment etc. As described in the afore-mentioned Applicant's co-pending applications, the conical portion 104 of the abutment 100 can engage the top surface of the implant in a tapered or sealed fit.

In one embodiment, the abutment 100 has a beveled transition surface 180 between the shaped portion 102 and the conical portion 104. The transition surface 180 has an outer edge 182 that is configured to be positioned at approximately the same height as the top surfaces of the naturally occurring soft-tissue morphology and an inner edge 183. The outer edge 182 is adjacent the conical portion 104 while the inner edge 183 is adjacent the shaped portion 102. Both the outer edge 182 and the inner edge 183 have a curved or scalloped shape that define at least one and more preferably two transition peaks 184, a transition buccal valley 186 and a transition lingual valley 187 that follow or at least closely approximate the shape of the naturally occurring contours of a patient's soft-tissue morphology. The transition buccal valley 186 is configured to face the cheek and the transition lingual valley 187 is configured to face the tongue. It should also be appreciated that in other embodiments, the transition peaks 184 and transition valleys 186 and 187 may be approximated by various combinations of straight and/or curved lines that are configured to follow or at least closely approximate the shape of the naturally occurring contours of a patient's bone-tissue morphology.

In some embodiments, the transition peaks 184 lie approximately 2-7 millimeters above the apical end 101 of the abutment 100. In other embodiments, the transition peaks 184 lie between approximately 4-5 millimeters or about 4.5 millimeters above the apical end 101 of the abutment 100. In some embodiments, the transition buccal valley 186 lies approximately 2-4 millimeters above the apical end 101 of the abutment 100. In other embodiments, the transition buccal valley 186 lies about 3 millimeters above the apical end 101 of the abutment 100. In some embodiments, the transition lingual valley 187 lies about 3-5 millimeters above the apical end 101 of the abutment 100. In other embodiments, the transition lingual valley 187 lies about 4 millimeters or about 3.8 millimeters above the apical end 101 of the abutment 100.

As illustrated in FIGS. 2A and 2B, the transition buccal valley 186 is more apical than the transition lingual valley 187. That is, a lowest point on the transition buccal valley 186 is more apical than a lowest point of the transition lingual valley 187. In other embodiments, the transition lingual valley 187 can be more apical than the transition buccal valley 186. In addition, as illustrated in FIG. 2B, both the curvatures of the outer edge 182 and inner edge 183 between the transition peak 184 and the transition lingual valley 187 and the curvatures of the outer edge 182 and inner edge 183 between the transition peak 184 and transition buccal valley 186 are convex in shape. As illustrated in FIG. 2B, in some embodiments the transition peaks 184 are located about in the middle between the transition buccal valley 186 and the transition lingual valley 187. In other embodiments, the transition peaks 184 can be located closer to either the transition buccal valley 186 or the transition lingual valley 187. This configuration of the outer edge 182 and the inner edge 183 of the transition surface 180 result in an asymmetrical abutment 100 that is well suited for matching asymmetrical soft-tissue morphologies, resulting in an aesthetically pleasing abutment 100. Although not illustrated it should be appreciated that in modified embodiments the peaks and valleys may have different heights. That is, the two peaks may have different heights as compared to each other. In a similar manner, the two valleys may have different heights as compared to each other.

As best seen in FIG. 2D, an inner bore 110 can extend through the center of the abutment 100. The inner bore 110 can be divided into a first and second region 112 and 114. The first region 112 can comprise a diameter that is slightly larger than the diameter of the second region 114. Accordingly, a seat 116 can be formed between the first and second regions 112 and 114. This seat 116 can support a coupling member. An embodiment of a coupling member is described in Applicant's co-pending applications, U.S. application Ser. No. 11/739,034 filed on Apr. 23, 2007, entitled "DENTAL IMPLANT" and U.S. application Ser. No. 11/739,024 filed on Apr. 23, 2007, entitled "DENTAL IMPLANT AND DENTAL COMPONENT CONNECTION," the entirety of which are also incorporated herein by reference. The second region 114 can include internal capture threads 118 that are configured to interface with the coupling member.

Figure 2F:
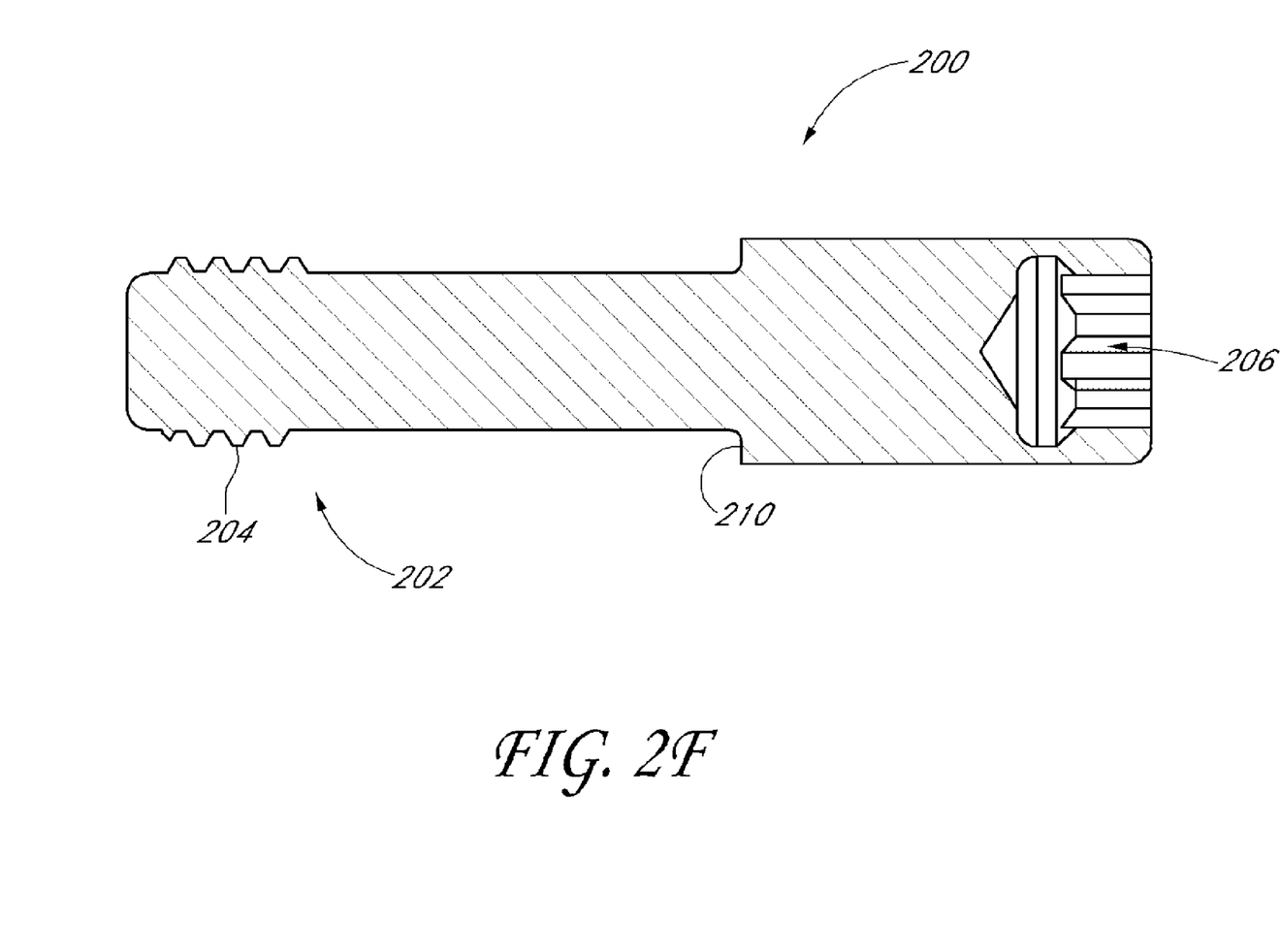
FIG. 2F is a cross-sectional view of a coupling member.

FIG. 2F illustrates an embodiment of a coupling member or screw 200 that can be used mechanically couple the abutment 100 to the implant 20. The coupling member 200 can also be made of a dental grade titanium alloy, although other suitable materials can be used. The coupling member 200 can be sized and shaped to extend through the inner bore 110 of the abutment 100 and into the cavity 66 of the implant 20. The coupling member 200 can include an externally threaded lower region 202 that engages the internal capture threads 118 of the abutment 100 and engages the threaded chamber 70 of the implant 20. The threads 204 of the coupling member 200 can engage the capture threads 118 so that the coupling screw 200 does not become disassociated as the abutment 100 is transferred and lifted into a patient's mouth.

The coupling member or screw 200 also includes a recess 206 in a shape configured to receive a Unigrip® rotational tool provided by Nobel Biocare™. In other embodiments, the recess 206 can have a different shape, such as, for example, a hexagon configured to allow for the insertion of a hexagonally shaped tool such as a conventional Allen® wrench to install or remove the coupling screw 200 from the implant 20.

Figure 3A:
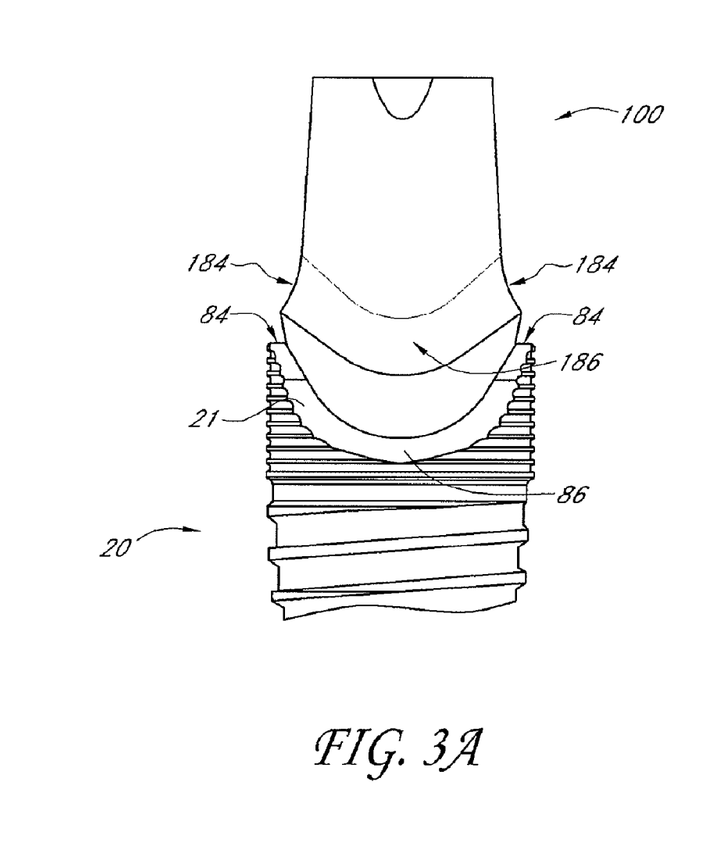
FIG. 3A is a front view of the abutment of FIG. 2A mated with the implant of FIG. 1A.
Figure 3B:
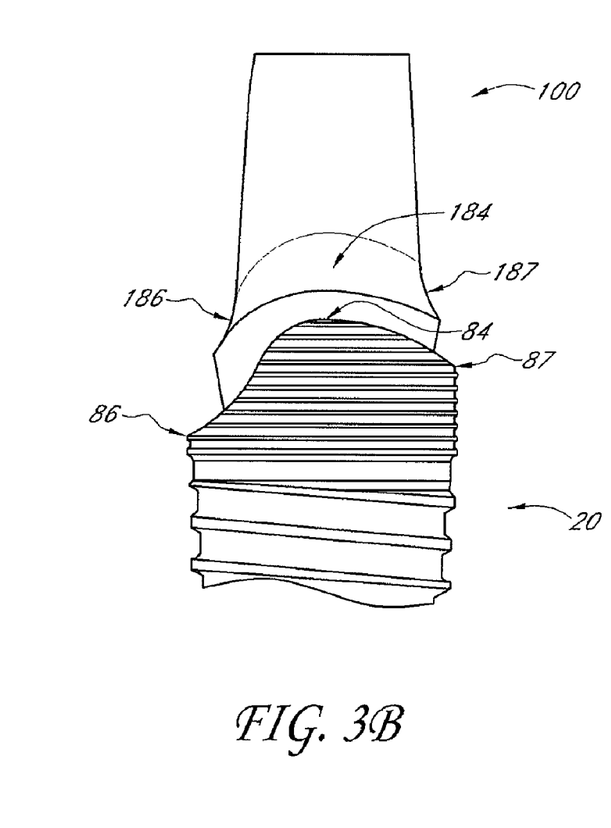
FIG. 3B is a side view of the abutment and implant of FIG. 3A.

To couple the abutment 100 to the dental implant 20 with the coupling screw 200, the interlock portion 106 of the abutment 100 is aligned and inserted into the interlock recess 74 of the dental implant 20. Furthermore, the conical portion 104 of the abutment 100 is inserted into the conical chamber 68 of the dental implant 20. The abutment 100 can be inserted into the cavity 66 of the dental implant 20 such that the lower end 108 of the interlock portion 106 is in contact with the lower end 75 of the interlock recess 74. The top surface 21 of the implant 20 can remain exposed when the abutment 100 is coupled to the implant 20, as illustrated in FIGS. 3A and 3B. In one embodiment, the exposed top surface 21 has thickness of at least about 0.2 millimeters and in one embodiment a thickness of about 0.25 millimeters. Advantageously, top surface 21 can form a "horizontal" tissue apposition surface, that can be provided with a bone apposition surface 41 as described above. This arrangement encourages uniform tissue growth above the bone tissue.

The apical threaded region 202 of the coupling screw 200 can be engaged with the threaded chamber 70 of the dental implant 20 and the seat 210 of the coupling screw 200 is abutting the seat 116 of the abutment 100. This engagement of the coupling screw 200 and the abutment 100 and the dental implant 20 can thereby secure the abutment 100 to the dental implant 20. As illustrated in FIGS. 3A and 3B, the peaks 84 and the valleys 86 and 87 of the dental implant 20 are aligned with the transition peaks 184 and transition valleys 186 and 187 of the abutment 100.

Figure 4A:
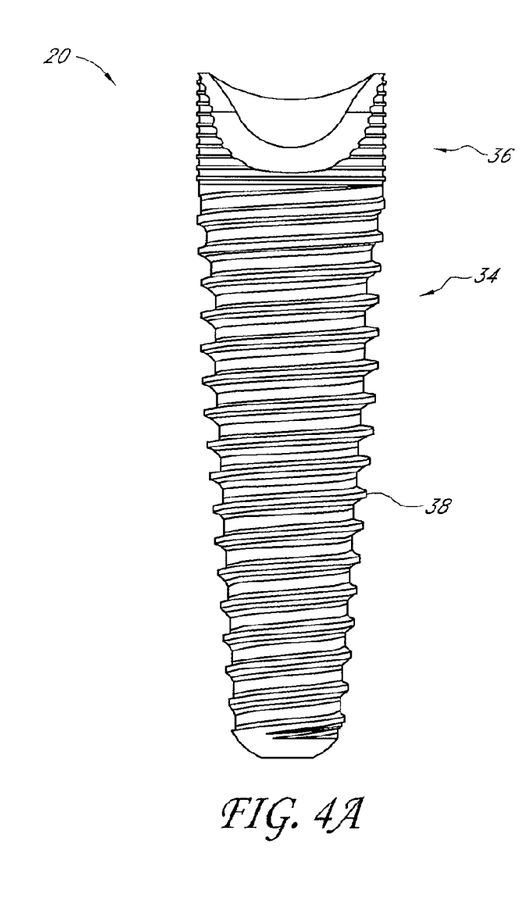
FIG. 4A is a front view of a conical dental implant in accordance with an embodiment of the present invention.
Figure 4B:
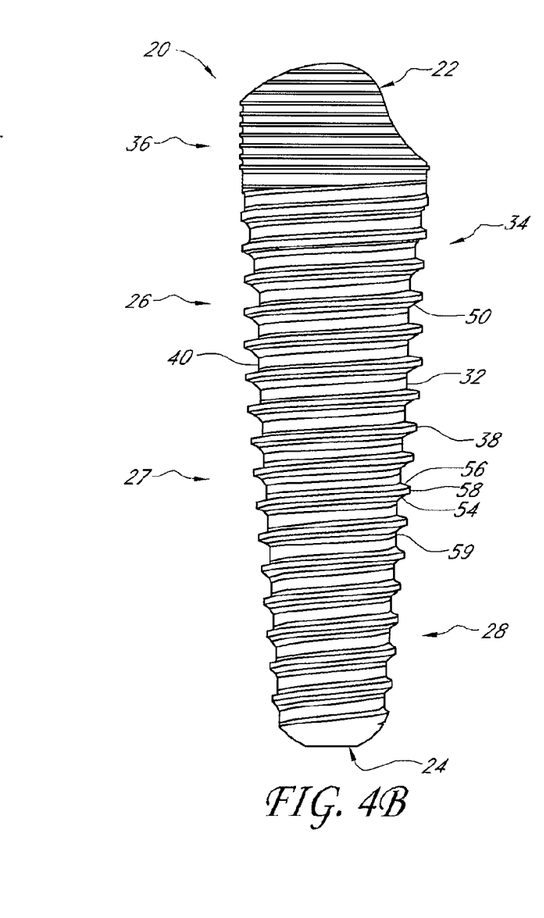
FIG. 4B is a side view of the conical dental implant of FIG. 4A.

FIGS. 4A and 4B illustrate an embodiment of a dental implant 20 that is similar to the dental implant 20 described above. The implant 20 comprises an implant body 32, which includes a threaded portion 34 and a collar 36. The threaded portion 34 can be tapered and can include at least one thread 38 that is located on an outer surface 40 of the threaded portion 34. The thread 38 comprises an apical flank 54 and a coronal flank 56 that are connected by a face 58. The base of the thread comprises a thread root 59. As will be explained below, although the illustrated embodiment includes a thread 38 that extends helically around the implant, modified embodiments may include more threads (e.g., double or triple lead threads). In addition, as explained below, the body 32 is illustrated as being generally conical or tapered. The dental implant 20 can comprise a coronal end 22, a coronal portion 26 generally adjacent the coronal portion 22, a apical end 24 and a apical portion 28 generally adjacent the apical end 24, and a central portion 27 between the coronal portion 26 and the apical portion 28.

The threaded portion 34 also comprises grooves 50 that are located on the thread 38. The grooves 50 are located on the dental implant 20 to, e.g. provide additional surfaces for osseointegration. The grooves 50 can be located on the thread face 58, the thread root 59, the apical flank 54 or the coronal flank 56. In some embodiments, the grooves 50 are located between the thread 38. In general, the grooves 50 extend in a generally helical pattern. In the illustrated embodiment, each groove 50 is substantially continuous. However, in modified embodiments, at least some grooves 50 can be formed to be non-continuous. For example, the grooves 50 can be formed from a series of shorter grooves, dimples, or indentations that together form a generally helical pattern. However, continuous grooves can advantageously promote bone attachment as growth as it has been observed that bone tissue prefers to grow along continuous channels.

The embodiments described above provide for improved stability of a dental implant when implanted in the alveolar bone. Furthermore, certain embodiments of the invention provide efficient utilization of space. For example, as described above, in certain embodiments, the grooves 50 are located on the face 58 of the thread 38 at a portion of the body 32 containing the internal connection interface 66. Hence, the strength of the body of the implant 20 at this location remains unaffected. If the grooves 50 had been located on the body 32 at this portion, less space would have been available for the internal connection interface 66 with maintained minimum wall thickness at specific dimensions to maintain body strength. Hence, having the grooves 50 positioned at the face 58 in the portion of the internal connection interface 66 improves the space available for the connection interface 66 and still provides for improved stability of the implant 20. In some embodiments, the wall thickness will be sufficient if the grooves 50 are located at the face 58 only at the portion of the interlock recess 74 but at least partly not at the location of the threaded chamber 70.

In the portion of the body 32 that does not include the internal connection interface 66, the grooves 52 can be located on the body 32. This will not deteriorate the strength of the implant 20 substantially as the implant 20 of the illustrated embodiment does not include any internal connection interface 66 at this portion. This provides for the option of having a thinner face of the thread 38 at this location, such as a variable thread thickness, which may provide for even further improved stability of the implant 20. Hence, the location of the grooves 50 provides for stability themselves as well as their specific locations. In addition, efficient utilization of the space available without compromising strength is provided. The locations also provide for flexibility, as the locations for the grooves 50 can be used on implants having either an internal connection interface 66 or an external connection interface.

In some embodiments, the threaded portion 34 of the dental implant 20 can comprises two flutes that are positioned on the apical portion 28 of the dental implant 20. The flutes can be configured to aid in inserting the dental implant 20. The flutes can comprise a generally helical shape. Further, the flutes can extend from the apical end 24 toward a generally central portion of the dental implant 20. The flutes can be located at generally opposing positions along the threaded portion 34 of the implant body 32. The flutes are configured to cut, or remove bone, when the dental implant 20 is rotated in a counterclockwise direction. Furthermore, the flutes are configured to allow the dental implant 20 to be rotated clockwise without cutting or removing bone. However, bone removal may be accomplished by rotating the implant counterclockwise.

Although the dental implant 20 has been described with flutes that are configured to cut when the dental implant 20 is rotated in a counterclockwise direction, other suitable flutes or flute orientations may also be used. Such suitable flutes or flute orientations may comprise flutes that are configured to cut or provide a tapping function when the dental implant 20 is rotated in a clockwise direction.

Figure 5A:
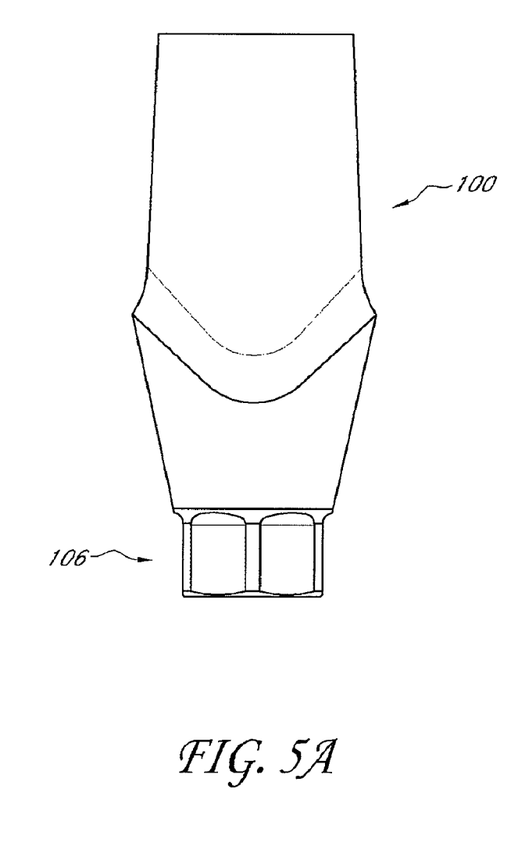
FIG. 5A is a front view of an embodiment of an abutment which is configured to mate with the implant of FIG. 4A.
Figure 5B:
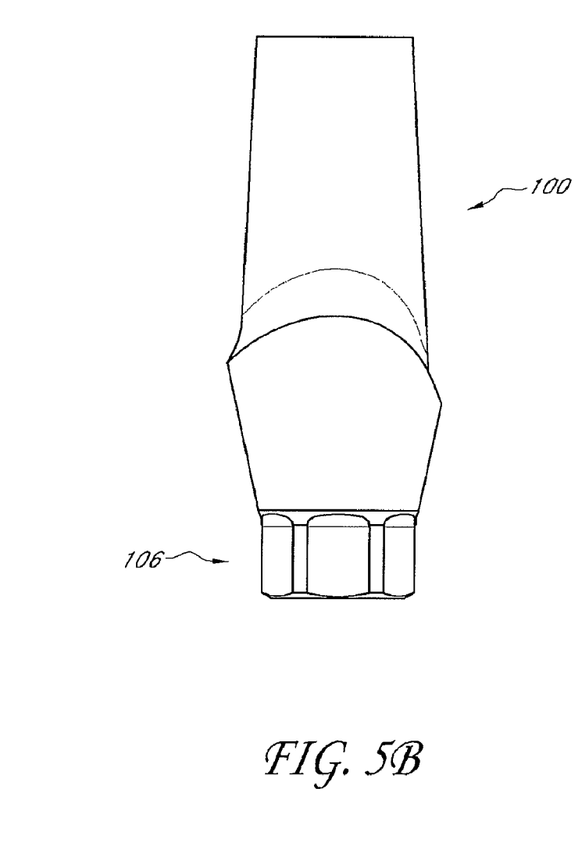
FIG. 5B is a side view of the abutment of FIG. 5A.

FIGS. 5A and 5B illustrate an embodiment of an abutment 100 that is configured to mate with the embodiment of the dental implant 20 illustrated in FIGS. 4A and 4B. This embodiment of the abutment 100 is similar to the embodiments described above. In this embodiment, a different variation of an interlock portion 106 is shown. In this embodiment, the interlock portion is hexagonal.

The portions of the implant 20 and abutment 100 that are exposed after implantation may be polished to reduce accumulation of plaque and calculus. In a modified embodiment, the some parts of the exposed portions proximate the soft-tissue may be treated to promote, enhance or maintain soft-tissue attachment. Such treatments may include applying growth factor, applying protein, roughening and/or the application of coatings that increase surface area. In other embodiments, treatments that increase surface area by taking off the existing surface may also be used, such as, for example, acid treatments, oxidized titanium surfaces etc. In addition, the soft tissue surface may be modified or covered with a coating that changes the color of the surface. For example, in one embodiment the surface is coated with a material hydroxyapatite (HA) or other ceramic coatings that are generally white or "tooth-like" in color.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while the number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combined with, or substituted for, one another in order to perform varying modes of the disclosed invention. Thus, it is intended that the scope of the present invention herein disclosed should not be limited by the particular disclosed embodiments described above, but should be determined only by a fair reading of the claims.

What is claimed is:

1. A dental implant for supporting a dental prosthesis, the implant comprising:
    a body comprising an outer surface, an apical end, and a coronal portion;
    at least one thread located on at least a threaded portion of the outer surface of the body, the thread comprising a coronal flank and an apical flank, the thread further comprising a face extending between the coronal flank and the apical flank; and
    a collar at the coronal portion of the dental implant, the collar comprising a curved surface defining a first peak, a second peak generally opposed to the first peak, a first valley between the first peak and the second peak, and a second valley between the first peak and the second peak and generally opposed to the first valley;
    wherein a most apical point of the first valley is more coronal than a most apical point of the second valley, wherein when viewed from a side along an axis passing through the first and second peaks, between the first and second peaks adjacent the first valley, the curved surface of the collar is only convex.

2. The dental implant of claim 1, wherein the curved surface between the second valley and the first peak is concave shaped.

3. The dental implant of claim 1 further comprising a helical groove formed on the outer surface of the body and located between the apical and coronal flanks.

4. The dental implant of claim 1, comprising a first groove having a helical pattern, the first groove being formed on at least a portion of an apical flank of the thread.

5. The dental implant of claim 1 further comprising a cavity located at least partially in the coronal portion of the body, the cavity being open towards the coronal end of the dental implant and configured to attach an abutment.

6. The dental implant of claim 5, wherein the cavity comprises at least one surface that tapers inwardly to form a substantially conical portion that extends from a top surface of the implant.

7. The dental implant of claim 6, wherein the substantially conical portion defines a conical half angle with respect to a longitudinal axis of the implant between about 10 degrees and about 20 degrees.

8. The dental implant of claim 6, wherein the substantially conical portion defines a conical half angle with respect to the longitudinal axis of the implant of about 12 degrees.

9. The dental implant as in claim 6, wherein the substantially conical portion has a length measured from the top surface in a direction along a longitudinal axis that is equal to or greater than at least about 1 mm.

10. The dental implant of claim 6, further comprising an interlock recess comprising at least one flat side positioned below the substantially conical portion.

11. The dental implant of claim 10, wherein the ratio of the length of the conical portion and the length of the interlock portion is about 1:1.

12. The dental implant of claim 6, further comprising an interlock recess that includes at least one anti-rotational feature positioned apical to the substantially conical portion, and a threaded portion that includes a thread positioned below the interlock recess.

13. The dental implant of claim 1, further comprising a plurality of substantially horizontally extending grooves on the collar.

14. The dental implant of claim 1, wherein the curved surface of the collar at the second valley is oriented at an angle relative to the longitudinal axis.

15. The dental implant of claim 1, wherein the curved surface of the collar at the first valley is oriented at an angle relative to the longitudinal axis.

16. The dental implant of claim 1, wherein the curved surface of the collar at the first and second peaks is oriented normal relative to the longitudinal axis.

17. The system of claim 1, wherein the curved surface of the collar at the first and second valleys is oriented at an angle relative to the longitudinal axis and wherein the curved surface of the collar at the first and second peaks is oriented normal relative to the longitudinal axis.

18. A system for replacing a tooth, the system comprising:
    a dental implant having a body comprising an outer surface, an apical end, and a coronal portion;
    at least one thread located on at least a threaded portion of the outer surface of the body, the thread comprising a coronal flank and an apical flank, the thread further comprising a face extending between the coronal flank and the apical flank; and a collar at the coronal portion of the dental implant, the collar comprising a curved surface defining a first peak, a second peak generally opposed to the first peak, a first valley between the first peak and the second peak, and a second valley between the first peak and the second peak and generally opposed to the first valley; wherein the first valley has a most apical point that is more coronal than a most apical point of the second valley, wherein when viewed from a side along an axis passing through the first and second peaks, between the first and second peaks adjacent the first valley, the curved surface of the collar is only convex; and an abutment configured to be coupled to the dental implant, the abutment having an elongate body comprising a coronal portion, an apical portion, an apical end, and an interlock portion at the apical end, and a transition surface between the coronal portion and the apical portion; wherein the transition surface defines a first transition peak, a second transition peak generally opposed to the first transition peak, a first transition valley between the first transition peak and the second transition peak, and a second transition valley between the first transition peak and the second transition peak and generally opposed to the first transition valley; wherein the first transition valley has a most apical point that is more coronal than a most apical point of the second transition valley.

19. The system of claim 18, wherein the curved surface of the collar at the second valley is oriented at an angle relative to the longitudinal axis.

20. The system of claim 18, wherein the curved surface of the collar at the first valley is oriented at an angle relative to the longitudinal axis.

21. The system of claim 18, wherein the curved surface of the collar at the first and second peaks is oriented normal relative to the longitudinal axis.

22. The system of claim 18, wherein the curved surface of the collar at the first and second valleys is oriented at an angle relative to the longitudinal axis and wherein the curved surface of the collar at the first and second peaks is oriented normal relative to the longitudinal axis.

\* \* \* \* \*